(12) United States Patent
Mearns et al.

(10) Patent No.: US 9,192,469 B2
(45) Date of Patent: Nov. 24, 2015

(54) DEVICES AND METHODS FOR LOADING A PROSTHESIS ONTO A DELIVERY SYSTEM

(71) Applicant: Medtronic Ventor Technologies Ltd., Minneapolis, MN (US)

(72) Inventors: Paul Mearns, Headford (IE); John Gallagher, Dublin (IE); Kevin O'Sullivan, Tarlee (IE); Mark Casley, Galway (IE); Pat Duane, Barna (IE)

(73) Assignee: Medtronic Ventor Technologies Ltd., Minneapolis, MN (US)

( * ) Notice: Subject to any disclaimer, the term of this patent is extended or adjusted under 35 U.S.C. 154(b) by 0 days.

(21) Appl. No.: 14/058,643

(22) Filed: Oct. 21, 2013

(65) Prior Publication Data

US 2014/0067053 A1    Mar. 6, 2014

Related U.S. Application Data

(62) Division of application No. 12/912,479, filed on Oct. 26, 2010, now Pat. No. 8,562,663.

(51) Int. Cl.
*A61F 2/24* (2006.01)
*A61F 2/95* (2013.01)

(52) U.S. Cl.
CPC ............ *A61F 2/2427* (2013.01); *A61F 2/2412* (2013.01); *A61F 2/2418* (2013.01); *A61F 2002/9522* (2013.01); *A61F 2220/0075* (2013.01); *Y10T 29/53843* (2015.01)

(58) Field of Classification Search
CPC ... A61F 2/2412; A61F 2/2418; A61F 2/2427; A61F 2002/9522; A61F 2220/0075
USPC .................. 623/1.12, 1.2, 2.1, 2.11, 2.18
See application file for complete search history.

(56) References Cited

U.S. PATENT DOCUMENTS

| | | | |
|---|---|---|---|
| 5,626,604 A | 5/1997 | Cottone, Jr. |
| 5,672,169 A | 9/1997 | Verbeek |
| 5,931,851 A | 8/1999 | Morales |
| 5,951,540 A | 9/1999 | Verbeek |
| 5,992,000 A | 11/1999 | Humphrey et al. |
| 6,009,614 A | 1/2000 | Morales |
| 6,018,857 A | 2/2000 | Duffy et al. |
| 6,024,737 A | 2/2000 | Morales |
| 6,051,002 A | 4/2000 | Morales |
| 6,063,092 A | 5/2000 | Shin |
| 6,063,102 A | 5/2000 | Morales |
| 6,068,635 A | 5/2000 | Gianotti |

(Continued)

FOREIGN PATENT DOCUMENTS

EP    0941713    9/1999

*Primary Examiner* — Ashley Fishback

(57) ABSTRACT

A method for loading a prosthesis onto a delivery system includes passing a distal end of a delivery system through a first open end and a second open end of a reducing member. The method includes seating the prosthesis in a piston member of a cap by contacting a first end of the prosthesis with a first surface of the piston member and by contacting a portion of a side of the prosthesis with at least one side wall extending from the periphery of the first surface. Additionally, the method includes inserting the distal end of the delivery system into a center of the prosthesis and an opening defined by the piston member. And the method includes advancing the cap towards a reducing member such that a portion of the prosthesis seated in the piston member advances along an inner surface of the conical wall of the reducing member.

9 Claims, 16 Drawing Sheets

(56) References Cited

U.S. PATENT DOCUMENTS

| | | |
|---|---|---|
| 6,360,577 B2 | 3/2002 | Austin |
| 6,629,350 B2 | 10/2003 | Motsenbocker |
| 6,925,847 B2 | 8/2005 | Motsenbocker |
| 2003/0225445 A1 | 12/2003 | Derus |
| 2004/0148007 A1 | 7/2004 | Jackson et al. |
| 2006/0173537 A1 | 8/2006 | Yang et al. |
| 2007/0056346 A1 | 3/2007 | Spenser et al. |
| 2007/0239271 A1 | 10/2007 | Nguyen |
| 2008/0058916 A1 | 3/2008 | Huang et al. |
| 2008/0071362 A1 | 3/2008 | Tuval et al. |
| 2009/0018570 A1 | 1/2009 | Righini et al. |
| 2009/0093876 A1 | 4/2009 | Nitzan et al. |
| 2010/0036484 A1 | 2/2010 | Hariton et al. |
| 2010/0121434 A1 | 5/2010 | Paul et al. |
| 2012/0083874 A1* | 4/2012 | Dale et al. .......... 623/2.11 |

* cited by examiner

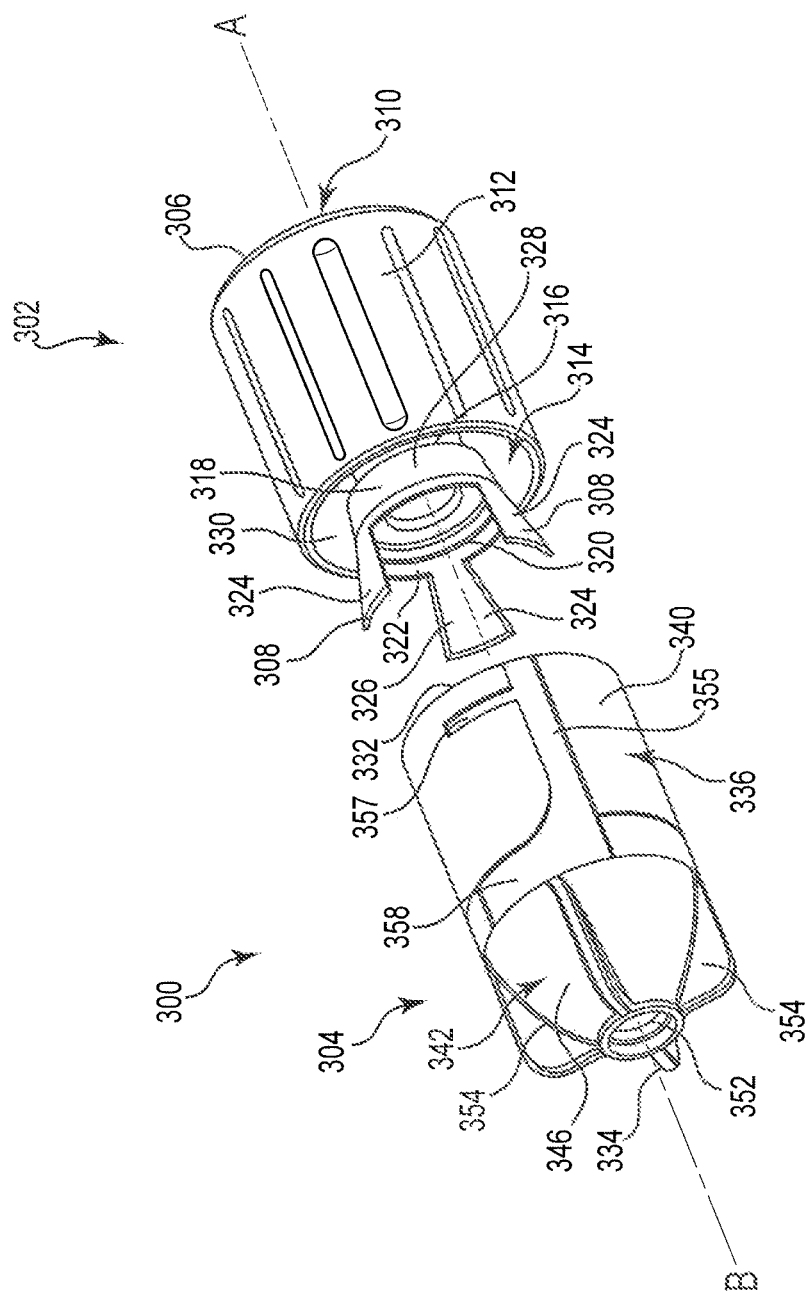

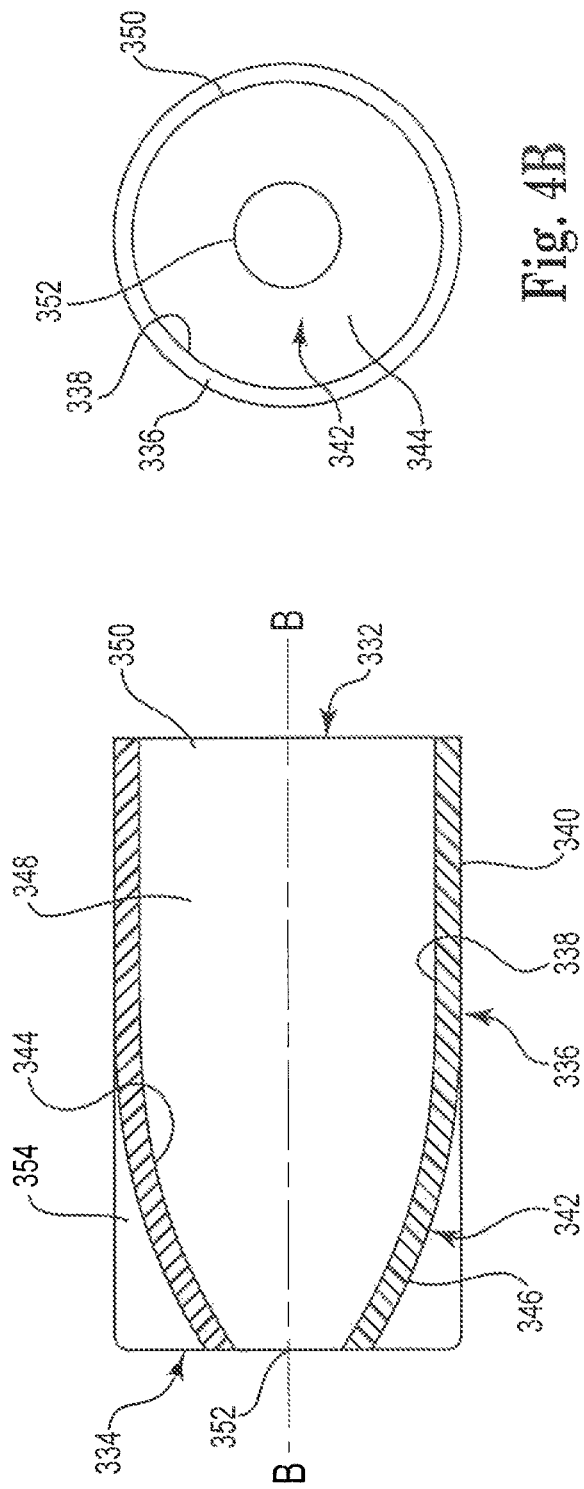

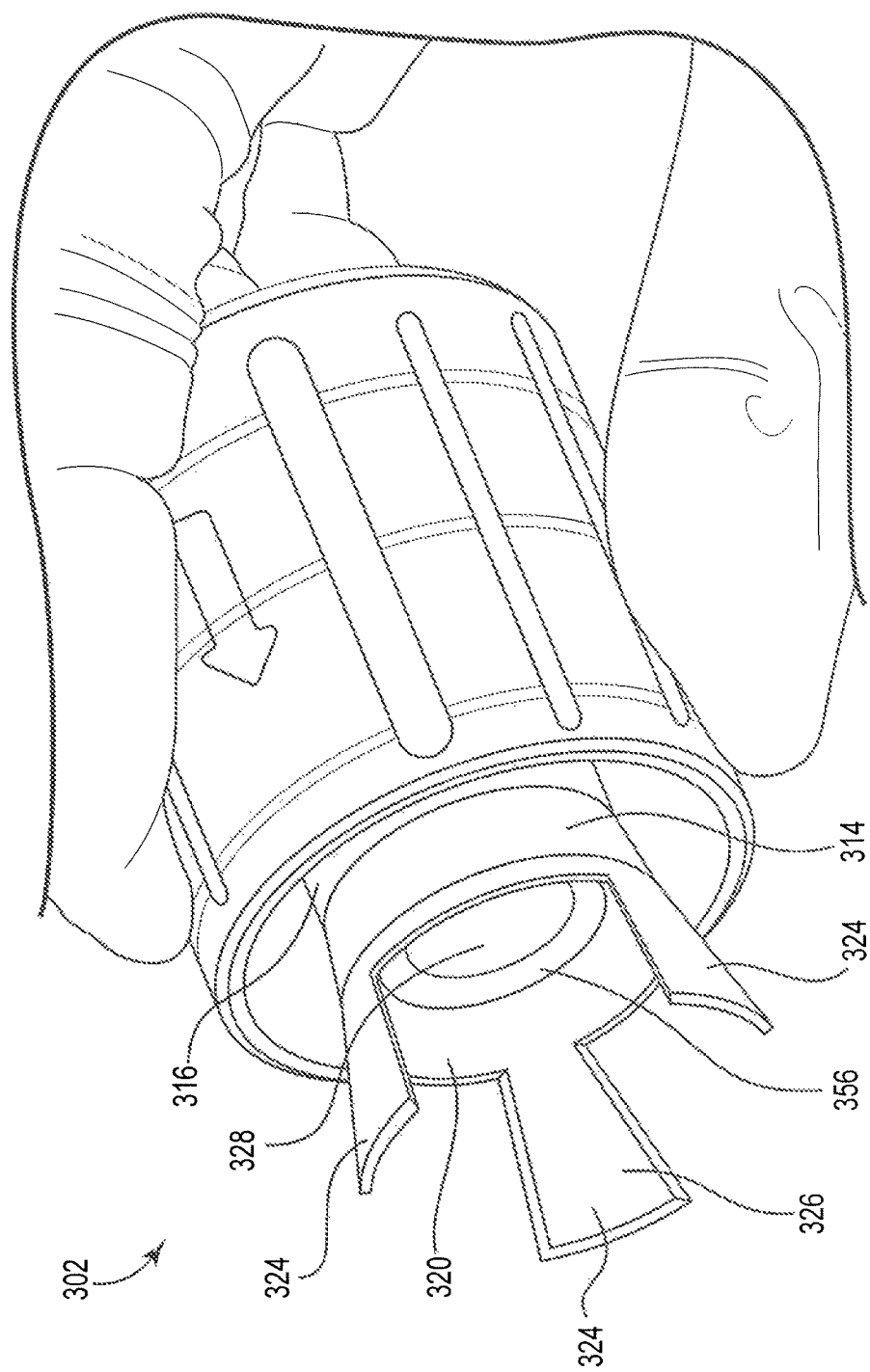

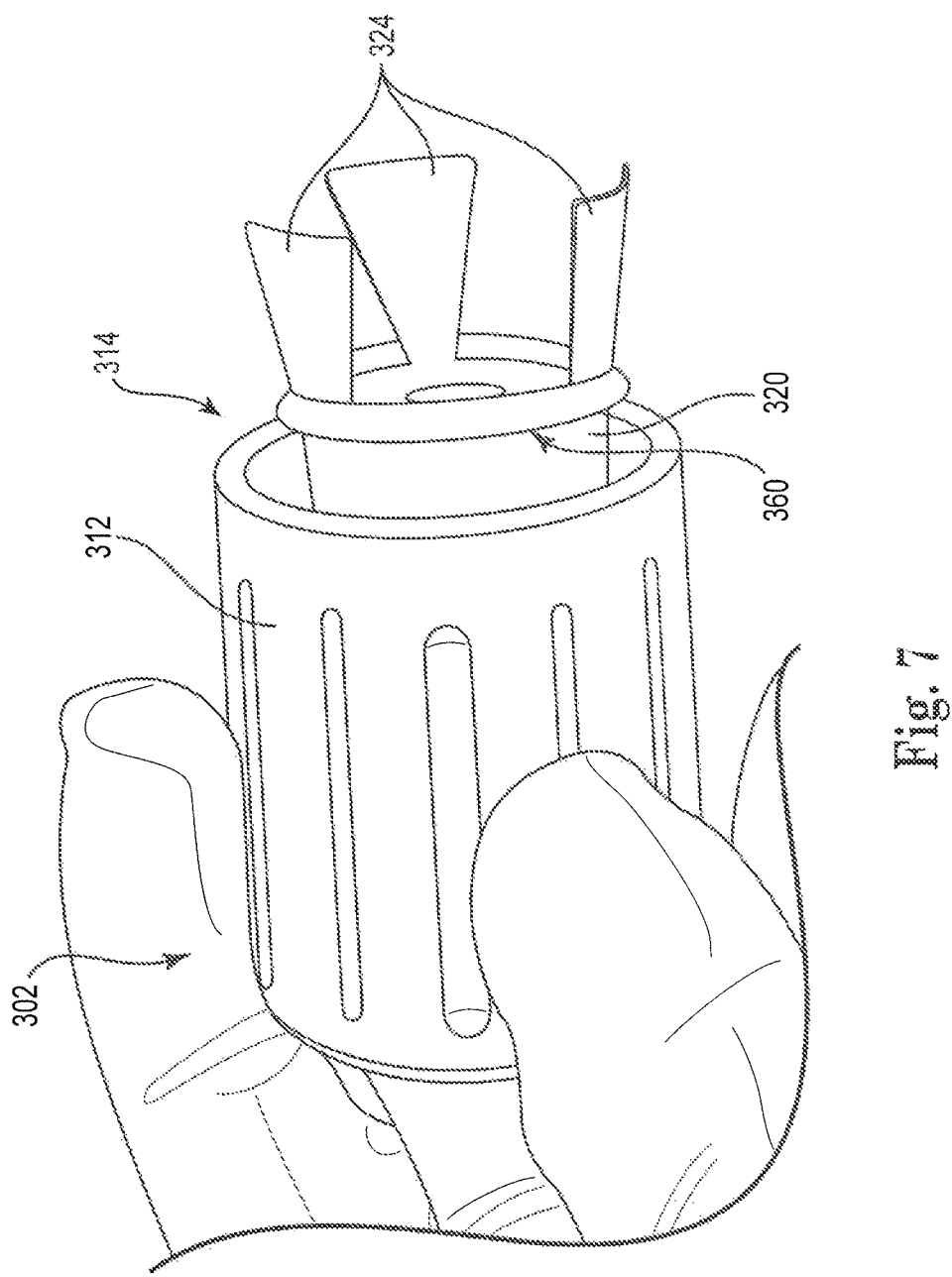

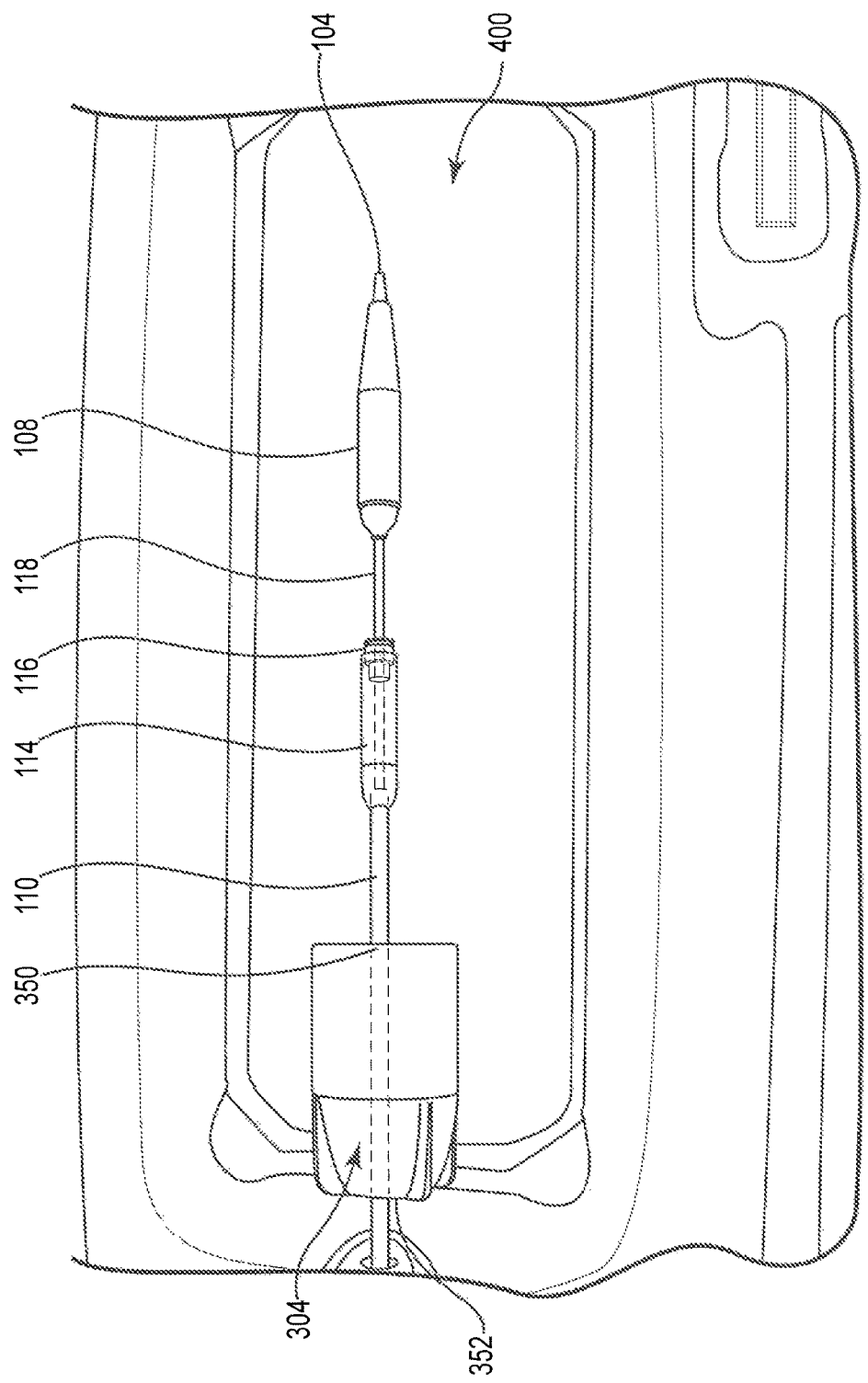

DEVICES AND METHODS FOR LOADING A PROSTHESIS ONTO A DELIVERY SYSTEM

CROSS-REFERENCE TO RELATED APPLICATION

This application is a divisional of U.S. application Ser. No. 12/912,479, filed Oct. 26, 2010, which is incorporated by reference in its entirety.

BACKGROUND

1. Field

The present invention relates to devices and methods for loading a prosthesis onto a delivery system and, particularly, to devices and methods for loading a valve prosthesis onto a minimally invasive delivery system, for example, a delivery catheter.

2. Background

The replacement of a deficient cardiac valve is often performed by opening a patient's thorax, placing the patient under extracorporeal circulation or peripheral aorto-venous heart assistance, temporarily stopping the heart, surgically opening the heart, excising the deficient valve, and then implanting a prosthetic valve in its place. This procedure has the disadvantage of requiring prolonged patient hospitalization, as well as extensive and often painful recovery. It also presents advanced complexities and significant costs.

To address the risks associated with open-heart implantation, minimally invasive approaches have been developed to facilitate catheter-based implantation of valve prostheses in the heart, including a beating heart. For example, a valve prosthesis formed by attaching a valve to a frame made of a wire or a network of wires has been proposed. Such a valve prosthesis can be contracted radially to introduce the valve prosthesis into the body of the patient percutaneously through a catheter.

To prepare such a valve prosthesis for implantation, the valve prosthesis can be initially provided in an expanded or uncrimped condition, then crimped or compressed around the distal tip of the catheter assembly until the valve prosthesis is as close to or smaller than the diameter of the distal tip as possible. Various methods and devices are available for crimping the valve prosthesis onto the catheter's distal tip, which may include hand-held devices or tabletop devices, for example.

Loading, a valve prosthesis on the delivery system, however, can be difficult as the valve prosthesis and crimping device must be carefully inserted over the distal tip of the catheter assembly without damaging the valve or frame, including, for example, support arms of the valve prosthesis. Accordingly, a need exists for a device and method of loading prosthesis onto a delivery system, such as a delivery catheter, that reduces the risk of damage to the prosthesis during loading.

BRIEF SUMMARY

The present invention relates generally to devices and methods for loading a prosthesis, for example, a valve prosthesis, onto a delivery system such as a delivery catheter for a minimally invasive implantation of the prosthesis. Although preferred embodiments of the loading device are used with self-expanding prostheses, the present invention can be used with balloon-expandable or other mechanically-expanded prostheses. Preferred embodiments of the present invention permit the reduction of an external dimension of a compressible prosthesis without damaging the prosthesis.

In an embodiment, a device for loading a prosthesis onto a delivery system comprises a cap and a reducing member. The cap has a piston member. The piston member includes a first surface that is configured to contact one end of a prosthesis seated therein. The piston member also includes at least one side wall extending from the periphery of the first surface. The side wall is configured to contact a portion of the side of the prosthesis seated therein. The reducing member has a conical wall, a first open end, and a second open end. The first open end is configured to receive the piston member. The reducing member reduces an external dimension of at least a portion of the prosthesis seated in the piston member as the prosthesis is moved along an inner surface of the conical wall. In another embodiment, the reducing member also includes a cylindrical wall that defines the first open end, and wherein the conical surface defines the second open end.

In an embodiment, a method for loading a prosthesis onto a delivery system comprises passing a distal end of a delivery system through a first open end and a second open end of a reducing member; seating the prosthesis in a piston member of a cap, which contacts a portion of a side of the valve prosthesis with at least one side wall extending from the piston member; inserting the distal end of the delivery system into the center of the valve prosthesis and an opening defined by the piston member; and advancing the valve prosthesis retained in the piston member along an inner surface of a conical wall of the reducing member towards the first open end of the reducing member. In another embodiment, the method includes coupling the other end of the valve prosthesis to a valve retainer of the delivery system, and advancing a valve retainer sleeve, over portions of the valve prosthesis that have been advanced along the conical wall of the reducing member.

Additional features of the invention will be set forth in the description that follows. Both the foregoing general description and the following detailed description are exemplary and explanatory and are intended to provide further explanation of the invention as claimed.

BRIEF DESCRIPTION OF THE FIGURES

The accompanying figures, which are incorporated herein, form part of the specification and illustrate exemplary embodiments of the present invention. Together with the description, the figures further serve to explain the principles of and to enable a person skilled in the relevant art(s) to make and use the exemplary embodiments described herein. In the drawings like reference characters indicate identical or functionally similar elements.

FIG. 3 illustrates a loading device having a cap and a reducing member according to an embodiment of the present invention.

FIG. 4A illustrates a cross section of the reducing member of FIG. 3 through the center of the reducing member.

FIG. 4B illustrates the reducing member of FIGS. 3-4A from the distal end of the reducing member.

FIG. 5 illustrates an alternate embodiment of a cap according to the present invention.

FIG. 7 illustrates an alternate embodiment of a cap having an optional friction interface.

FIG. 8 illustrates the loading device at a stage of the loading process at which the distal tip assembly is inserted through the reducing member.

DETAILED DESCRIPTION

The following detailed description of the present invention refers to the accompanying figures that illustrate exemplary embodiments. Other embodiments are possible and may fall within the scope of the present invention. Modifications can be made to the exemplary embodiments described herein without departing from the spirit and scope of the present invention. Therefore, the following detailed description is not meant to be limiting. The operation and behavior of the exemplary embodiments presented are described with the understanding that various modifications and variations of the exemplary embodiments may be within the scope of the present invention.

Figure 1:
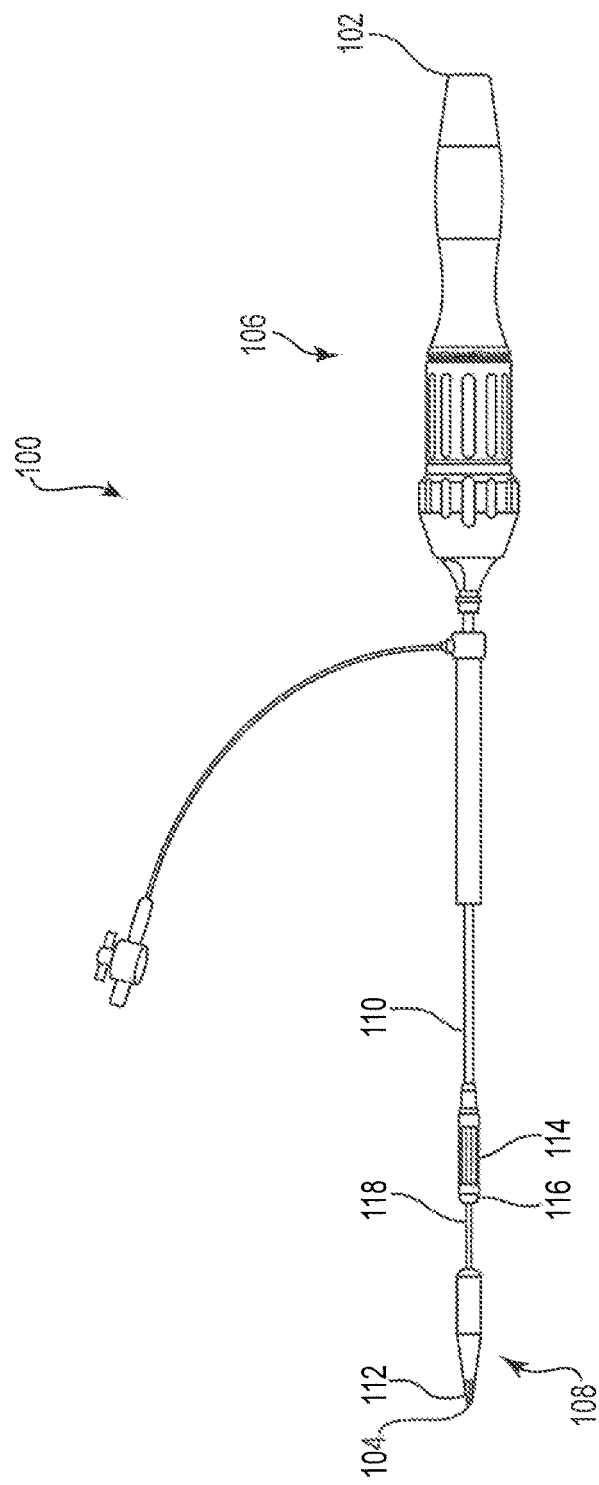
FIG. 1 illustrates an exemplary delivery system used with loading devices according to embodiments of the present invention.

FIG. 1 illustrates an exemplary embodiment of a catheter assembly 100. Catheter assembly 100 is described and illustrated herein to facilitate description of the loading devices according to embodiments of the present invention. Any number of alternate delivery systems, including other delivery catheters, can be used with the loading devices described herein. Catheter assembly 100 is merely exemplary.

Catheter assembly 100 has a proximal end 102 and a distal end 104. Catheter assembly 100 generally includes a handle assembly 106 located at proximal end 102, a distal tip assembly 108 located at distal end 104, and an outer delivery shaft 110 between distal tip assembly 108 and handle assembly 106. Outer delivery shaft 110 can retain a degree of flexibility. Distal tip assembly 108 includes a tip 112. Catheter assembly 100 can be advanced along a guide wire (not shown).

Figure 13:
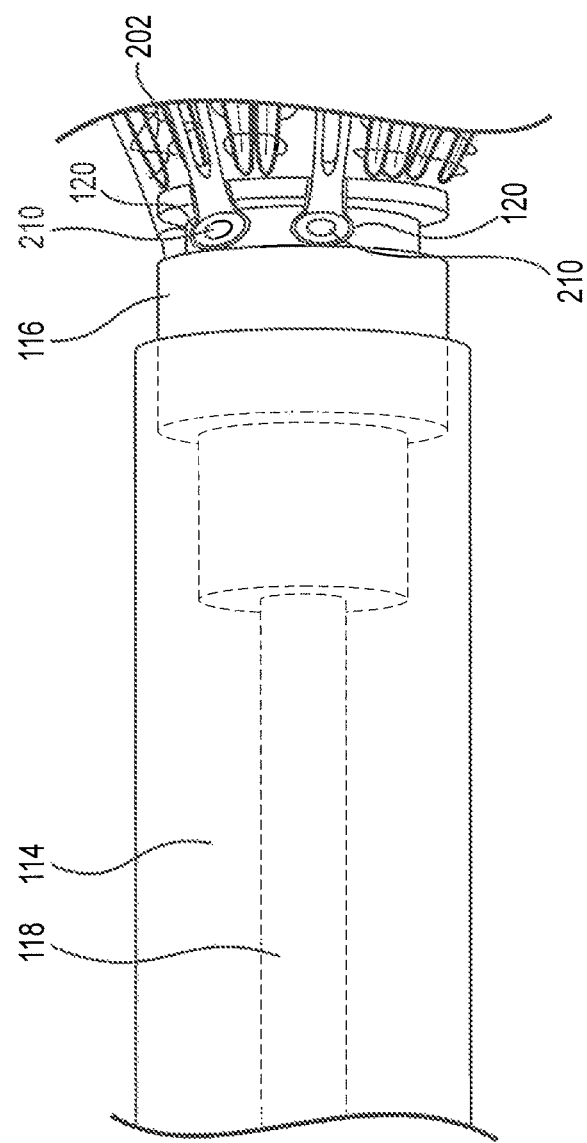
FIG. 13 illustrates the loading device at another stage of the loading process at which the valve prosthesis is coupled with the valve retainer.

Catheter assembly 100 further includes a valve retaining sleeve 114 and a valve retainer 116. Valve retaining sleeve 114 is coupled to the distal end of the outer delivery shaft 110. Valve retainer 116 is coupled to an intermediate delivery shaft 118. Valve retainer 116 can include a plurality of slots 120 at the distal end of valve retainer 116 as shown in FIG. 13. Outer delivery shaft 110 extends from the interior of handle assembly 106 to valve retaining sleeve 114. Tip 112 is coupled to the distal end of intermediate delivery shaft 118. Intermediate delivery shaft 118 extends from the interior of handle assembly 106 to tip 112, to which the distal end of intermediate delivery shaft 118 is coupled. Intermediate delivery shaft 118 is encompassed by outer delivery shaft 110 from the interior of handle assembly 106 until the outer delivery shaft 110 ends at valve retaining sleeve 114. Intermediate delivery shaft 118 is preferably a tubular member.

Figure 2:
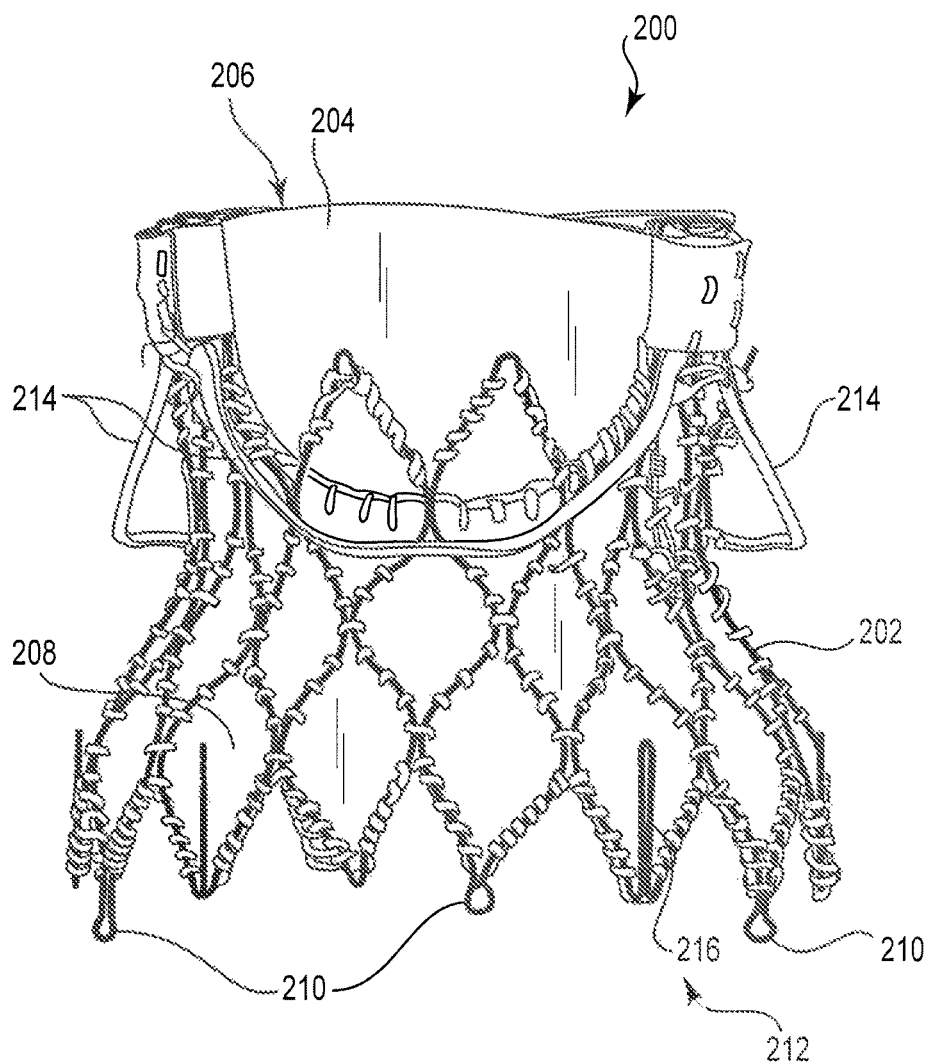
FIG. 2 illustrates an exemplary prosthesis that can be loaded onto a delivery system using loading devices according to embodiments of the present invention.

FIG. 2 illustrates an exemplary valve prosthesis 200. Valve prosthesis 200 is described and illustrated herein to facilitate description of the loading devices according to embodiments of the present invention. Any number of alternate prostheses can be used with the loading devices described herein. Valve prosthesis 200 is merely exemplary.

Valve prosthesis 200 includes support frame 202, valve leaflets 204 located towards the distal end 206 of valve prosthesis 200, and valve skirt 208. Support frame 202 includes coupling members 210 depending from a proximal end 212 of valve prosthesis 200. Support frame 202 is preferably formed of a self-expanding material, for example, nitinol. Other self-expanding or shape memory materials can be used instead of nitinol.

Preferably, three valve leaflets 204 are provided to form a tricuspid valve structure within valve prosthesis 200. Alternate valve leaflet configurations, for example, bicuspid valves, can be included in valve prostheses used with the loading devices and methods described herein. Valve leaflets 204 and skirt 208 can be formed from animal pericardium tissue, for example, bovine pericardium or porcine pericardium. In other embodiments, leaflets 204 and skirt 208 can be formed from synthetic materials. Leaflets 204 and skirt 208 are attached to support frame 202, preferably using sutures, as shown in FIG. 2. Alternately, various types of sutureless bonding methods can be used to attach leaflets 204 and skirt 208 to frame 202.

Coupling members 210 extend from proximal end 212 of support frame 202 and include eyelets or tabs at their proximal end. Coupling members 210, which are optional, can be formed in various configurations other than that shown. For example, coupling members 210 can be J-shaped hooks, or coupling members 210 can take on any number of sizes or shapes while remaining compatible with the loading devices and methods described herein.

Support frame 202 further includes three support arms 214 that can be attached to support frame 202 towards its distal end. Alternately, support arms 214 can be formed integrally with support frame 202. Support arms 214 are preferably formed of a self-expanding material, for example, nitinol. Other self-expanding or shape memory materials can be used instead of nitinol. Support arms 214 can be attached to support frame 202 such that they are biased away from support frame 202 but can pivot radially with respect to support frame 202. Support frame 202 can further include a plurality of barbs 216 towards the proximal end of support frame 202. Barbs 216 extend for a distance towards the distal end of support frame 202. Preferably, barbs 216 extend in an approximately axial direction. Barbs 216, which are optional, can also be biased or curved slightly inward, but with less inward curve than the surrounding section of support frame 202. Because the distal end of barbs 216 define a greater diameter than the surrounded support frame, barbs 216 receive the majority of forces when the proximal end of support frame 202 is loaded using the techniques described herein. This prevents damage to support frame 202 and, more particularly, to the sutures that attach skirt 208 to support frame 202.

FIGS. 3, 4A, and 4B illustrate a loading device 300 for loading a prosthesis frame onto a delivery system according to an embodiment of the present invention. Loading device 300 includes a cap 302 and a reducing member 304. Cap 302 has a distal end 306, a proximal end 308, and a longitudinal axis A. Cap 302 includes a circular base 310 at distal end 306. A cylindrical wall 312 extends from the periphery of base 310 towards proximal end 308. Preferably, cylindrical wall 312 extends axially with longitudinal axis A.

Cap 302 also includes a piston member 314. Piston member 314 is configured to seat valve prosthesis 200. Piston member 314 can include an elongate cylinder portion 316. Cylinder portion 316 extends from base 310 towards proximal end 308. Piston member 314 can also include a disc portion 318 at the proximal end of cylinder portion 316. Disc portion 318 has an outer diameter that is larger than the outer diameter of cylinder portion 316. In the illustrated embodiment, base 310, cylindrical portion 316, and disc portion 318 define an opening 328. Opening 328 can extend from distal end 306 of cap 300 to the proximal end of the disc portion 318 along longitudinal axis A.

Extending from the proximal end of the disc portion 318 is a cylindrical wall 320. Cylindrical wall 320 has a surface 322 at its proximal end. Piston member 314 can include at least one side wall 324. In the illustrated embodiment, piston member 314 includes three side walls 324. Side walls 324 extend from cylindrical wall 320 towards proximal end 308. Side walls 324 are preferably equally and circumferentially spaced around the periphery of cylindrical wall 320. As side walls 324 extend towards proximal end 308, side walls 324 preferably move away from longitudinal axis A. Side walls 324 are generally triangular—the width of side walls 324 at the proximal end is greater than the width of side walls 324 at the distal end. Each side wall 324 has an arcuate inner surface 326. Side walls 324 can be formed in other configurations. For example, side walls 324 can have a constant width, or side walls 324 can extend axially with longitudinal axis A. Piston member 314 can include one side wall, two side walls, or more than three side walls. For reasons discussed below, piston member 314 preferably includes a separate side wall 324 for each support arm 214 of valve prosthesis 200, and each side wall 324 is preferably sized to cover a majority of support arm 214.

Valve prosthesis 200 can be seated in the recess defined by the disc portion 318 and cylindrical wall 320 at the distal end, and the side walls 324 circumferentially. Preferably, valve prosthesis 200 is orientated such that distal end 206 faces piston member 314. Distal end 206 of valve prosthesis 200 is inserted against surface 322. An outer dimension of frame 202 of valve prosthesis 200 can be compressed or reduced prior to being seated in the piston member 314. For example, a portion of or the entire external dimension of prosthesis 200 may be reduced by hand, or otherwise, such that the outer dimension of the prosthesis 200 is at least slightly smaller than the recess defined by the proximal end of side walls 224.

Side walls 324 contact side portions of valve prosthesis 200. In an embodiment, side walls 324 contact and enclose, at least a portion of, support arms 214 of valve prosthesis 200. In the illustrated embodiment of valve prosthesis 200, support arms 214 are biased away from support frame 202. Preferably, as valve prosthesis 200 is inserted in the recess defined by the disc portion 318 and cylindrical wall 320 at the distal end, side walls 324 contact support arms 214. Side walls 324 gradually pivot support arms 214 radially inward towards support frame 202 as valve prosthesis 200 is inserted. Accordingly, side walls 324 guide and protect support arms 214 of valve prosthesis 200 during loading by covering at least a portion of support arms 214 and by reducing the external dimension of the support arms 214. This protection reduces the risk that support arms 214 will prolapse during loading.

Preferably, base 310, cylindrical wall 312, and piston member 314 are concentric with longitudinal axis A to define a chamber 330 between cylindrical wall 312 and piston member 314.

Reducing member 304 has a distal end 332, a proximal end 334, and a longitudinal axis B. Reducing member 304 can include a cylindrical wall 336. Cylinthical wall 336 has an inner surface 338 (shown in FIGS. 4A and 4B) and an outer surface 340. Preferably, cylindrical wall 336 is axial with longitudinal axis B.

Reducing member 304 can include a conical wall 342. In the illustrated embodiment, conical wall 342 is connected to the proximal end of cylindrical wall 336. Conical wall 342 has an inner surface 344 (shown in FIGS. 4A and 4B) and an outer surface 346. The inner diameter of conical wall 324 decreases toward proximal end 334. As best illustrated in FIG. 4A, inner surface 344 has a curved profile. Alternately, inner surface 344 can have a planar profile. Reducing member 304 can also include a plurality of tabs 354. Tabs 354 extend radially from conical wall 342 to allow a user to securely grasp reducing member 304 and to prevent rotation thereof during loading.

Cylindrical wall 336 and conical wall 342 define a chamber 348 (shown in FIGS. 4A and 4B). Chamber 348 can have a first open end 350 defined by cylindrical wall 336 and a second open end 352 defined by conical wall 342. First open end 350 is sized to accept piston member 314 of cap 302 and a valve prosthesis 200 seated in piston member 314. Second open end 352 is sized to allow at least a portion of proximal end 212 of valve prosthesis 200 to protrude through second open end 352 when valve prosthesis 200 is inserted in chamber 348.

The chamber 330 of cap 302 is sized to accept the cylindrical wall 336 of reducing member 304 as the proximal end 308 of cap 302 is advanced within chamber 348. In this position, outer surface 340 of cylindrical wall 336 faces the inner surface of cylindrical wall 312. When the distal end of cylindrical wall 336 of reducing member 304 contacts base 310 of cap 302, advancement of piston member 314 within chamber 348 is stopped at a desired final position within chamber 348 of reducing member 304. As piston member 314 advances within chamber 348, the portion of valve prosthesis 200 that is proximal to and unenclosed by side walls 324 contacts the inner surface 344 of conical wall 342, compressing or reducing the outer diameter of valve prosthesis 200. Preferably, in the final position, the coupling members 210 are protruding from second open end 352 of reducing member 304.

In an embodiment, cap 302 can be selectively coupled with reducing member 304. Any suitable means of connection between cap 302 and reducing member 304 may be used. In the embodiment illustrated in FIG. 3, cylindrical wall 336 defines longitudinal notch 355, a first circumferential notch 357, and a second circumferential notch 358. Longitudinal notch 355, first circumferential notch 357, and second circumferential notch 358 are configured to receive two projections (not shown) formed on the inner surface of cylindrical wall 312. Cap 302 can be coupled to reducing member 304 by rotating cap 302 relative to reducing member 304. Other suitable means of connection may include corresponding threads or a frictional fit, for example.

Figure 6B:
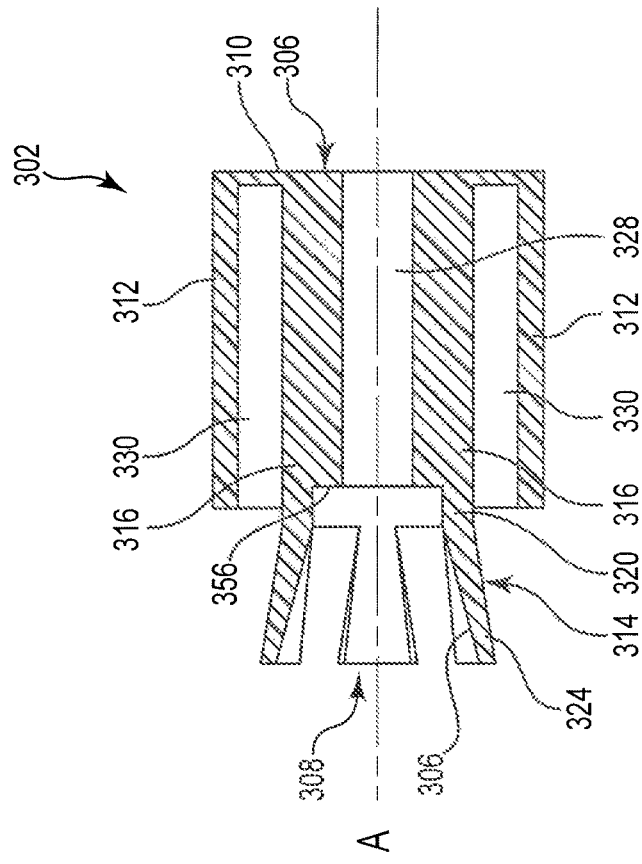
FIG. 6B illustrates a cross section of the cap of FIGS. 5-6A through the center of the cap.
Figure 6A:
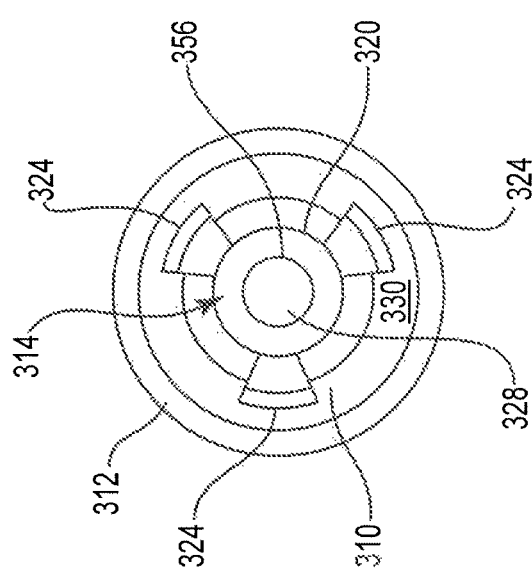
FIG. 6A illustrates the cap of FIG. 5 from the proximal end of the cap.

FIGS. 5, 6A, and 6B illustrate an alternate embodiment of piston member 314. Piston member 314 includes cylinder portion 316 that extends from base 310. Cylindrical wall 320, however, extends directly from the periphery of cylinder portion 316, defining a surface or lip 356. Side walls 324 extend from cylindrical wall 320 as described above. This embodiment omits disc portion 318. Valve prosthesis 200 can be seated in the recess defined by lip 356, cylindrical wall 320, and side walls 324. Preferably, valve prosthesis 200 is orientated such that distal end 206 faces piston member 314. Distal end 206 of valve prosthesis 200 is inserted against lip 356.

FIG. 7 illustrates an alternate embodiment of cap 302 having an optional friction interface surface. In the illustrated embodiment, piston member 314 further includes an O-ring 360. O-ring 360 encircles side walls 324 at the distal end, near cylindrical wall 320. At least a portion of the inner surface of O-ring 360 extends into the recess defined by the cylindrical wall 320 and the side walls 324. The portions of the inner surface of O-ring 360 that extend into the recess define the optional friction interface surface. When valve prosthesis 200 is inserted into the recess, at least a portion of the outer surface of valve prosthesis 200, for example, a portion of frame 202, contacts the inner surface of O-ring 360 that extends into the recess. The contact between valve prosthesis 200 and O-ring 360 creates a friction interface that prevents valve prosthesis 200 from moving, including translation and rotation, while the exposed portion of valve prosthesis 200 contacts inner surface 344 of conical wall 342, compressing or reducing the outer diameter of valve prosthesis 200. O-ring 360 can be a polymeric material or any other material with a coefficient of friction sufficient to prevent valve prosthesis 200 from moving, and that is suitable for use in surgical procedures. Other suitable means for creating the friction interface surface can be used, including, for example, lining cylindrical wall 320 with a polymeric lining or inserting a polymeric washer in the recess defined by cylindrical wall 320.

FIGS. 8-16 illustrate methods of loading a valve prosthesis 200 onto a delivery system, for example, catheter assembly 100. In FIG. 8, distal end 104 of catheter assembly 100 is passed through reducing member 304 such that valve retaining sleeve 114, valve retainer 116, and distal tip assembly 108 pass through second open end 352 and first open end 350. Preferably, this step is performed in a saline bath 400 such that distal tip assembly 108 never leaves the saline solution in saline bath 400.

Figure 9:
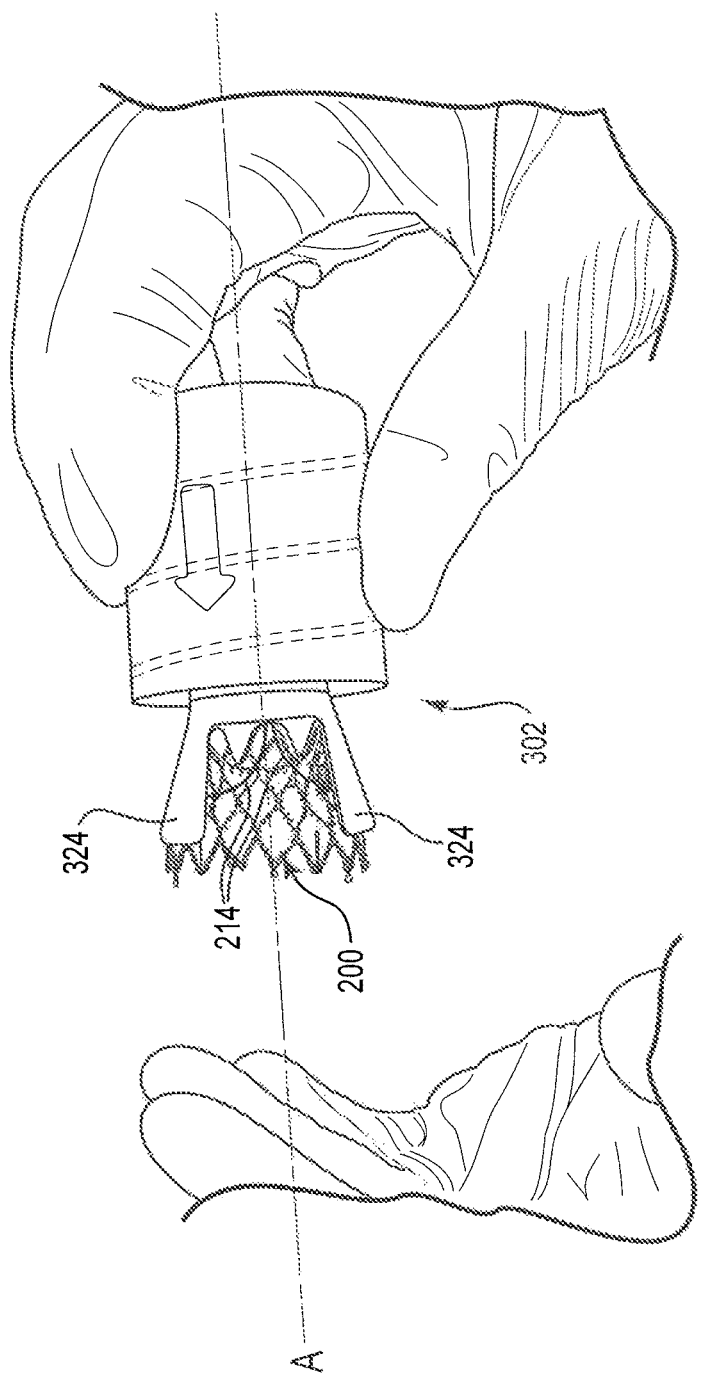
FIG. 9 illustrates the loading device at another stage of the loading process at which the valve prosthesis is seated in the cap.

In FIG. 9, valve prosthesis 200 is seated in piston member 314 of cap 302. This step can be performed inside or outside of saline bath 400. Valve prosthesis 200 is aligned with longitudinal axis A of cap 302 and oriented so distal end 206 of valve prosthesis 200 is facing piston member 314. Valve prosthesis is inserted in the recess defined, in part, by side walls 324 until the distal end 206 contacts a surface of piston member 314, for example, surface 322 or lip 356. A user can compress or reduce the outer dimension of frame 202 of valve prosthesis 200 prior to seating it in piston member 314. Support arms 214 are centered behind side walls 324 such that, at least, the apexes of support arms 214 are covered by side walls 324. Preferably, as valve prosthesis 200 is inserted in the recess, side walls 324 contact and radially pivot support arms 214 inward towards the center of valve prosthesis 200.

Figure 10:
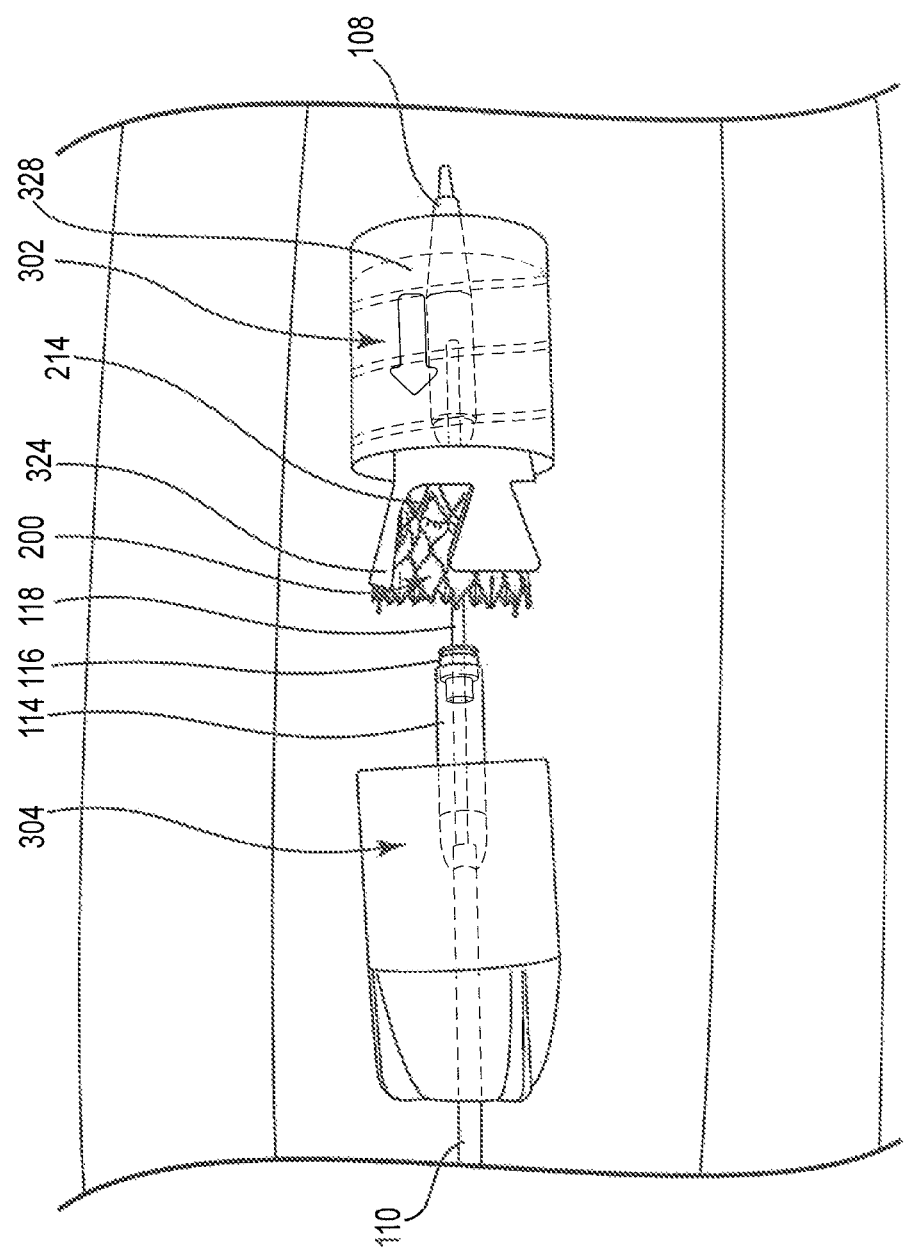
FIG. 10 illustrates the loading device at another stage of the loading process at which the cap and the valve prosthesis are inserted over the distal tip assembly.

In FIG. 10, cap 302 having valve prosthesis 200 seated in piston member 314 is placed over distal tip assembly 108. Distal tip assembly 108 is aligned with an opening defined by valve leaflets 204 of valve prosthesis 200 and opening 328 of cap 302, and advanced therein. In an embodiment, distal tip assembly 108 is advanced until at least a portion of distal tip assembly 108 protrudes through opening 328 at distal end 306 of cap 302. Preferably, this step is performed in saline bath 400.

Figure 11:
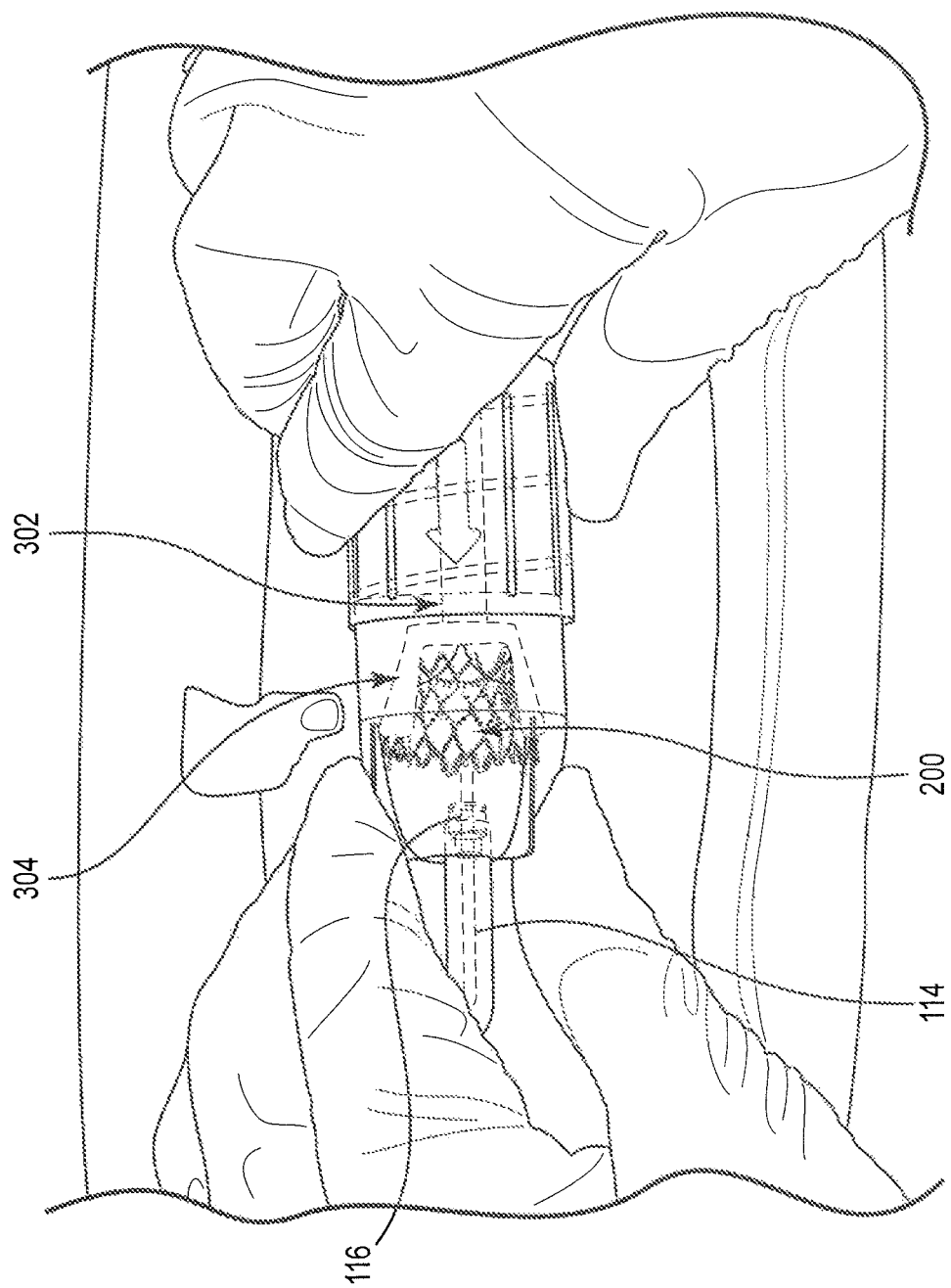
FIG. 11 illustrates the loading device at another stage of the loading process at which the cap is advanced towards the reducing member to crimp the valve prosthesis.
Figure 12:
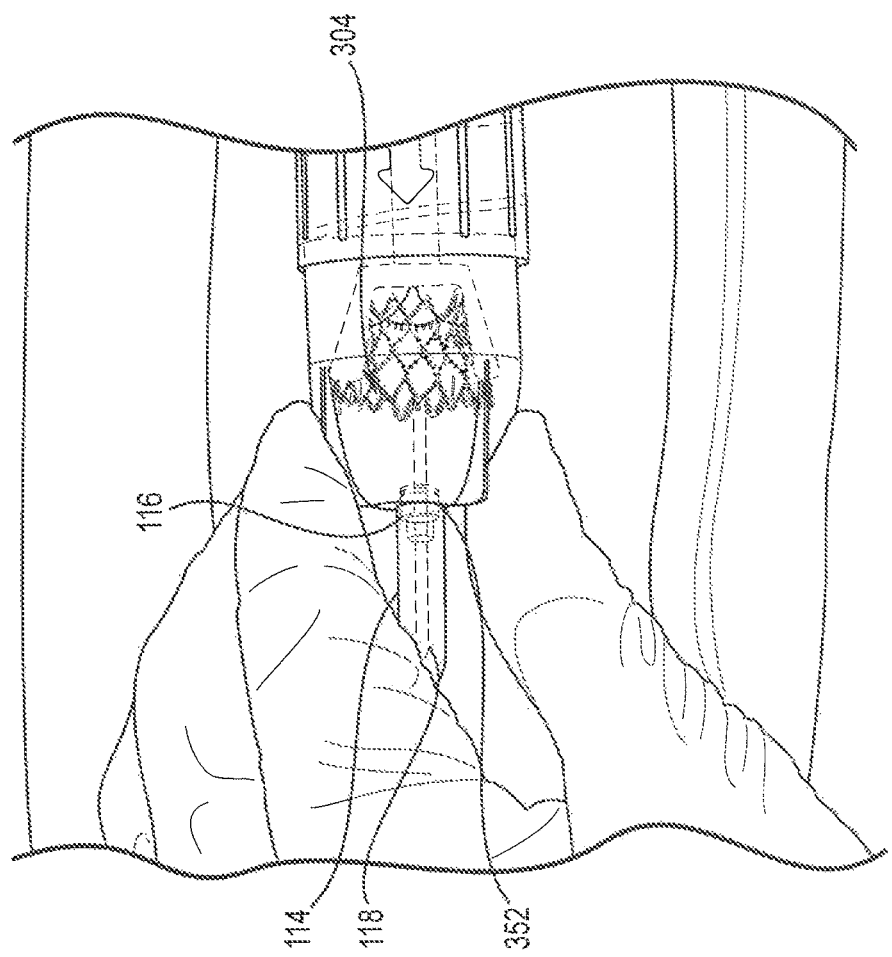
FIG. 12 illustrates the loading device at another stage of the loading process at which the reducing member is aligned with the valve retainer.

In FIG. 11, reducing member 304 is advanced toward cap 302 having valve prosthesis 200 seated therein. Reducing member 304 is advanced over piston member 314, causing the proximal end 212 of valve prosthesis 200 to slide along inner surface 344 of conical wall 342. As valve prosthesis 200 slides along, inner surface 344 towards second open end 352, the external dimension of the valve prosthesis 200 is reduced. Preferably, during this step, no air is present in loading device 300 to reduce the risk that flushing is impacted. Preferably, as shown in FIG. 12, proximal end 334 of reducing member 304 is radially aligned with catheter assembly 100 such that second open end 352 is aligned with the distal end of valve retainer 116. When cap 302 places valve prosthesis 200 in the final desired position, cap 302 is selectively coupled with reducing member 304. At this point, preferably, a portion of proximal end 216 of valve prosthesis 200 protrudes from second open end 352, including coupling members 210, for example.

In FIG. 13, valve prosthesis 200 is coupled to valve retainer 116. Coupling members 210, protruding from second open end 352, are inserted in slots 120 of valve retainer 116, preventing valve prosthesis 200 from moving apart from catheter assembly 100. Loading device 300 or catheter assembly 100 can be rotated to correctly align coupling members 210 with slots 120 for insertion.

Figure 14:
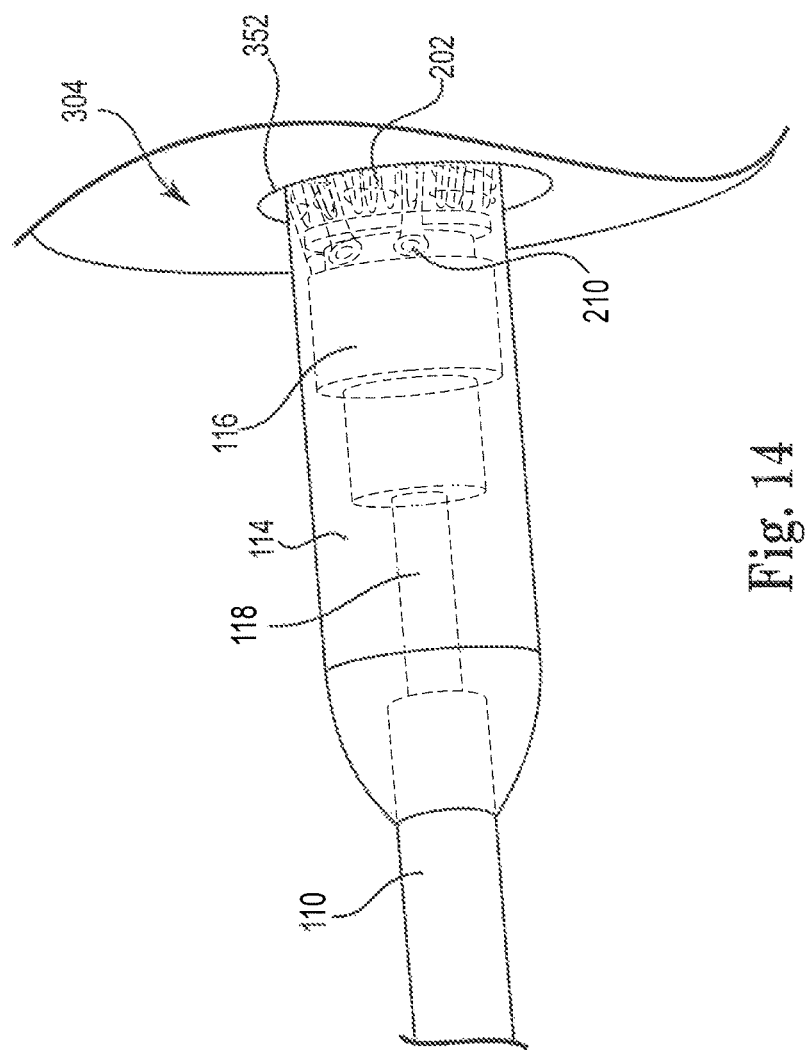
FIG. 14 illustrates the loading device at another stage of the loading process at which the valve retaining sleeve is advanced over the crimped portion of the valve prosthesis.
Figure 15:
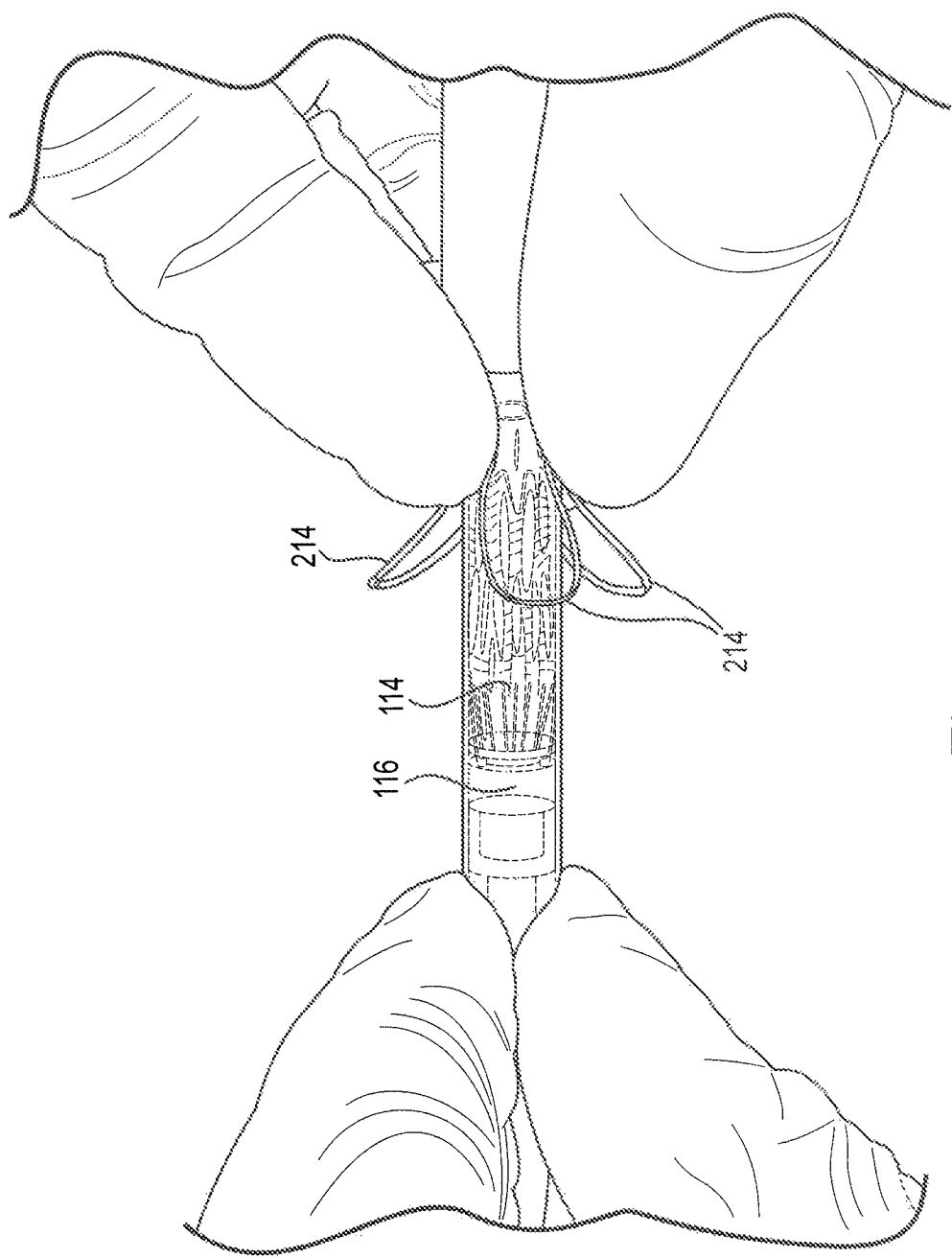
FIG. 15 illustrates the loading device at another stage of the loading process at which the valve prosthesis is loaded on the delivery system.

In FIG. 14, valve retaining sleeve 114 is advance over the proximal end 216 of valve prosthesis 200 that has a reduced external dimension. To advance valve retaining sleeve 114 over valve prosthesis 200, outer delivery shaft 110 and coupled valve retaining sleeve 114 can be extended over valve prosthesis 200, or alternately, intermediate delivery shaft 118 and coupled valve retainer 116 can be retracted within valve retaining sleeve 114. In an embodiment, valve retaining sleeve 114 is advanced over crimped portion of valve prosthesis 200 until the proximal end of valve retaining sleeve 114 is adjacent the proximal end of valve retainer 116. At this point, as illustrated in FIG. 15, valve retaining sleeve 114 encompasses the portion of frame 202 attached to the valve skirt 208, not encompassing support arms 214.

Figure 16:
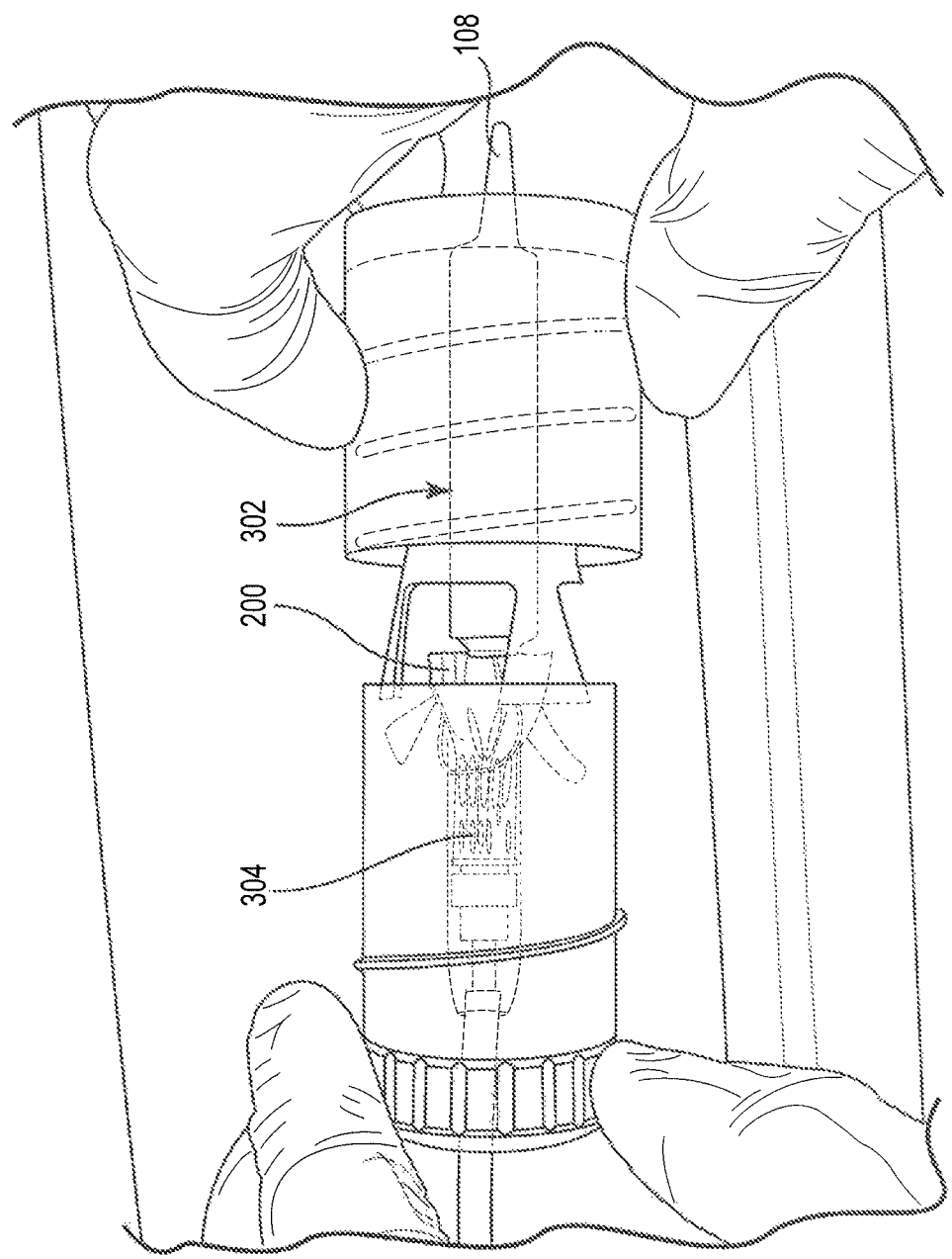
FIG. 16 illustrates the loading device at another stage of the loading process at which the cap is removed from the loaded valve prosthesis and reducing member.

In FIG. 16, cap 302 and reducing member 304 are uncoupled. Cap 302 is disengaged from valve prosthesis 200 and removed by advancing over distal tip assembly 108. At this point, valve prosthesis 200 is loaded on catheter assembly 100.

While various embodiments of the present invention have been described above, they have been presented by way of example only, and not limitation. The elements of the embodiments presented above are not necessarily mutually exclusive, but can be interchanged to meet various needs as would be appreciated by one of skill in the art.

It therefore will be apparent to one skilled in the art that various changes in form and detail can be made to the embodiments disclosed herein without departing from the spirit and scope of the present invention. The phraseology or terminology herein is used for description and not for limitation. Thus, it is intended that the present invention cover modifications and variations of this invention provided they come within the scope of the appended claims and their equivalents.

What is claimed is:

1. A method for loading a prosthesis onto a delivery system, the method comprising:

passing a distal end of a delivery system through a first open end and a second open end of a reducing member, the reducing member comprising a conical wall, the first open end being configured to receive a piston member of a cap;

seating the prosthesis in a recess defined by a first surface and at least one side wall extending from a periphery of the first surface of the piston member of the cap such that a first end of the prosthesis contacts the first surface of the piston member and such that an inner surface of the at least one side wall contacts an outer surface of a portion of a side of the prosthesis;

inserting the distal end of the delivery system into a center of the prosthesis and an opening defined by the piston member; and advancing the cap towards the reducing member such that a portion of the prosthesis seated in the piston member advances along an inner surface of the conical wall of the reducing member.

2. The method of claim 1, further comprising coupling the cap with the reducing member.

3. The method of claim 1, further comprising:

coupling a second end of the prosthesis to a prosthesis retainer of the delivery system; and advancing a retaining sleeve over at least a portion of the prosthesis that has been advanced along the conical wall of the reducing member.

4. The method of claim 3, further comprising advancing the piston member and the reducing member away from the prosthesis retained within the retaining sleeve.

5. The method of claim 3, wherein advancing the cap towards a reducing member further comprises advancing at least a portion of the second end of the prosthesis through the first open end of the reducing member.

6. The method of claim 5, wherein the at least a portion of the second end of the prosthesis comprises at least one coupling member, and wherein coupling the second end of the prosthesis to the prosthesis retainer comprises engaging each of the at least one coupling member with a slot in the prosthesis retainer.

7. The method of claim 3, wherein the prosthesis includes a frame and at least one support arm coupled to the frame and configured to pivot radially with respect to the frame, and wherein after the step of advancing the retaining sleeve over at least a portion of the prosthesis, the retaining sleeve encompasses the portion of the frame but does not encompass the at least one support arm.

8. The method of claim 1, wherein the prosthesis is a valve prosthesis having at least one support arm; and wherein seating the valve prosthesis in the recess centering the at least one support arm of the valve prosthesis with the at least one side wall of the piston member.

9. The method of claim 8, wherein the at least one side wall of the piston member comprises at least two side walls, and wherein the at least one support arm comprises at least two support arms.

* * * * *